United States Patent
Ho

(10) Patent No.: US 11,766,310 B2
(45) Date of Patent: Sep. 26, 2023

(54) SURGICAL ROBOT GOWN

(71) Applicant: AI Bioelectronic Healthtech Co., Ltd., Taoyuan (TW)

(72) Inventor: Yen-Yi Ho, Taoyuan (TW)

(73) Assignee: AI Bioelectronic Healthtech Co., Ltd., Taoyuan (TW)

(*) Notice: Subject to any disclaimer, the term of this patent is extended or adjusted under 35 U.S.C. 154(b) by 568 days.

(21) Appl. No.: 17/096,081

(22) Filed: Nov. 12, 2020

(65) Prior Publication Data
US 2021/0137185 A1 May 13, 2021

(30) Foreign Application Priority Data
Nov. 8, 2019 (TW) .............................. 108140680

(51) Int. Cl.
*A61B 90/98* (2016.01)
*G16H 40/67* (2018.01)
*A61B 34/30* (2016.01)
*A61B 46/10* (2016.01)

(52) U.S. Cl.
CPC .............. *A61B 90/98* (2016.02); *A61B 34/30* (2016.02); *A61B 46/10* (2016.02); *G16H 40/67* (2018.01)

(58) Field of Classification Search
CPC .................... A61B 90/98; A61B 46/10; A61B 34/30–34/37
See application file for complete search history.

(56) References Cited

U.S. PATENT DOCUMENTS

| 11,495,336 B2* | 11/2022 | Piron ..................... G06Q 30/04 |
| 2008/0281301 A1 | 11/2008 | DeBoer et al. |
| 2018/0096175 A1* | 4/2018 | Schmeling ............ G06F 1/3206 |
| 2018/0189449 A1* | 7/2018 | Karumba .............. H04L 9/3236 |
| 2019/0099232 A1 | 4/2019 | Soto et al. |
| 2019/0201141 A1 | 7/2019 | Shelton, IV et al. |
| 2021/0138456 A1 | 5/2021 | Ho |

FOREIGN PATENT DOCUMENTS

| DE | 102017105564 A1 | 11/2020 |
| EP | 3506298 A1 | 7/2019 |
| TW | I702398 B | 8/2020 |

* cited by examiner

*Primary Examiner* — Jonathan T Kuo

(57) ABSTRACT

A surgical robot gown applied to a surgical robot and electrically connected to a blockchain network is disclosed. The surgical robot includes a scalpel and a robotic arm. The surgical robot gown includes a waterproof gown, a chip set and a surgical time measuring unit. The waterproof gown covers the robotic arm, and the scalpel is exposed to the outside via the waterproof gown. The chip set is located on the waterproof gown, and including a blockchain tracer for recording the data of executing the surgery in the blockchain network for tracing. The surgical time measuring unit is located on the waterproof gown and electrically connected to the chip set, for measuring a surgery time of the surgical robot.

8 Claims, 3 Drawing Sheets

SURGICAL ROBOT GOWN

BACKGROUND OF THE INVENTION

1. Field of the Invention

The present invention relates to a surgical robot gown; more particularly, the present invention relates to a surgical robot gown that can prevent the surgical robot from being damaged by body fluid splashing during the surgery.

2. Description of the Related Art

With the development of medical technology and the precision requirements of minimally invasive surgery, manufacturers have developed surgical robots. Surgical robots have the characteristics of high stability, flexible operation, precise movement, and no mental fatigue. Therefore, many hospitals use surgical robots to undergo surgery.

However, the structure of the surgical robot is a confidential machine. During the operation, the patient's body fluid may splash on the surgical robot, which may cause rust and damage to the parts of the surgical robot over time. Therefore, it is necessary to provide a kind of gown that can prevent the surgical robot from being damaged by body fluid splashing during the operation.

SUMMARY OF THE INVENTION

The main purpose of the present invention is to provide a surgical robot gown that can prevent the surgical robot from being damaged by body fluid splashing during the operation.

In order to achieve the above-mentioned purpose, a surgical robot gown of the present invention is applied to a surgical robot and electrically connected with a blockchain network. The surgical robot includes a scalpel and a robotic arm. The surgical robot gown includes a waterproof gown, a chip set and an operation time measuring unit. The waterproof gown covers the robotic arm and exposes the scalpel from the waterproof gown to the outside. The chip set is arranged on the waterproof gown, and includes a blockchain tracer for recording the surgery data in the blockchain network for tracing. The surgical time measuring unit is arranged on the waterproof gown and electrically connected to the chip set for measuring a surgery time of the surgical robot.

According to an embodiment of the present invention, the chip set further includes an electronic tag element, which records the information of the surgical robot gown by means of radio frequency identification.

According to an embodiment of the present invention, the surgical robot gown further includes a wireless module, which is arranged on the waterproof gown and electrically connected to the chip set, the surgical time measuring unit and an external computer.

According to an embodiment of the present invention, the surgical robot gown further includes a battery, which is arranged on the waterproof gown and provides power to the chip set, the surgical time measuring unit and the wireless module.

According to an embodiment of the present invention, the waterproof gown further includes a cuff, from which the scalpel is exposed to the outside.

According to an embodiment of the present invention, the waterproof gown is made of thermoplastic urethane (TPU).

According to an embodiment of the present invention, the operation time includes an operation start time and an operation end time.

According to an embodiment of the present invention, the data of the operation performed by the surgical robot includes a power-on time, a power-off time, a type of surgery, and a patient data.

DETAILED DESCRIPTION OF THE PREFERRED EMBODIMENT

Figure 1:
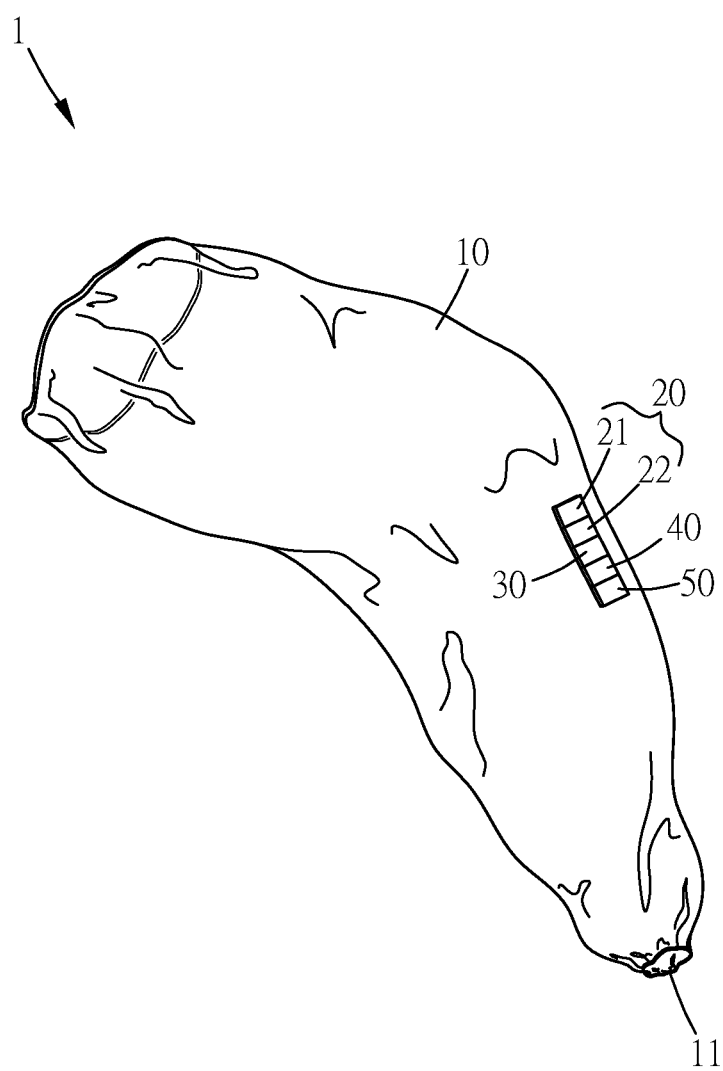
FIG. 1 is a schematic diagram of a surgical robot gown in an embodiment of the present invention.
Figure 2:
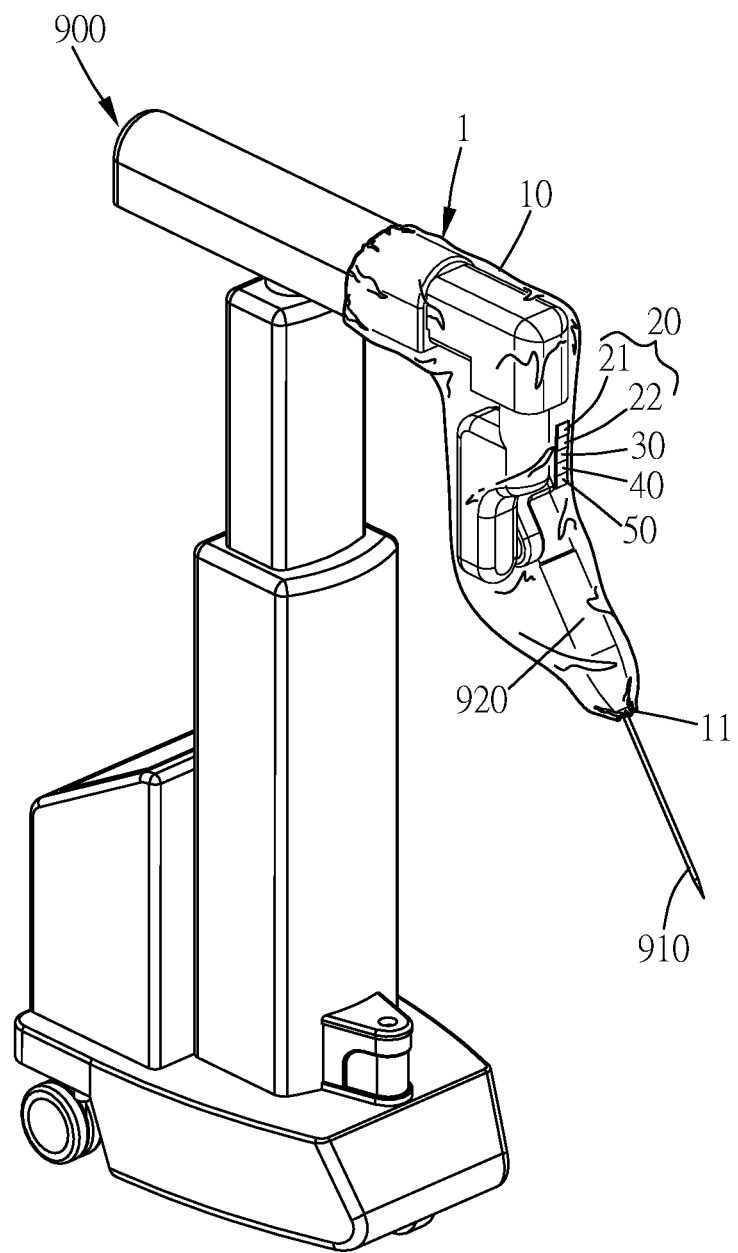
FIG. 2 is a schematic diagram of the surgical robot gown applied to the surgical robot in an embodiment of the present invention.
Figure 3:
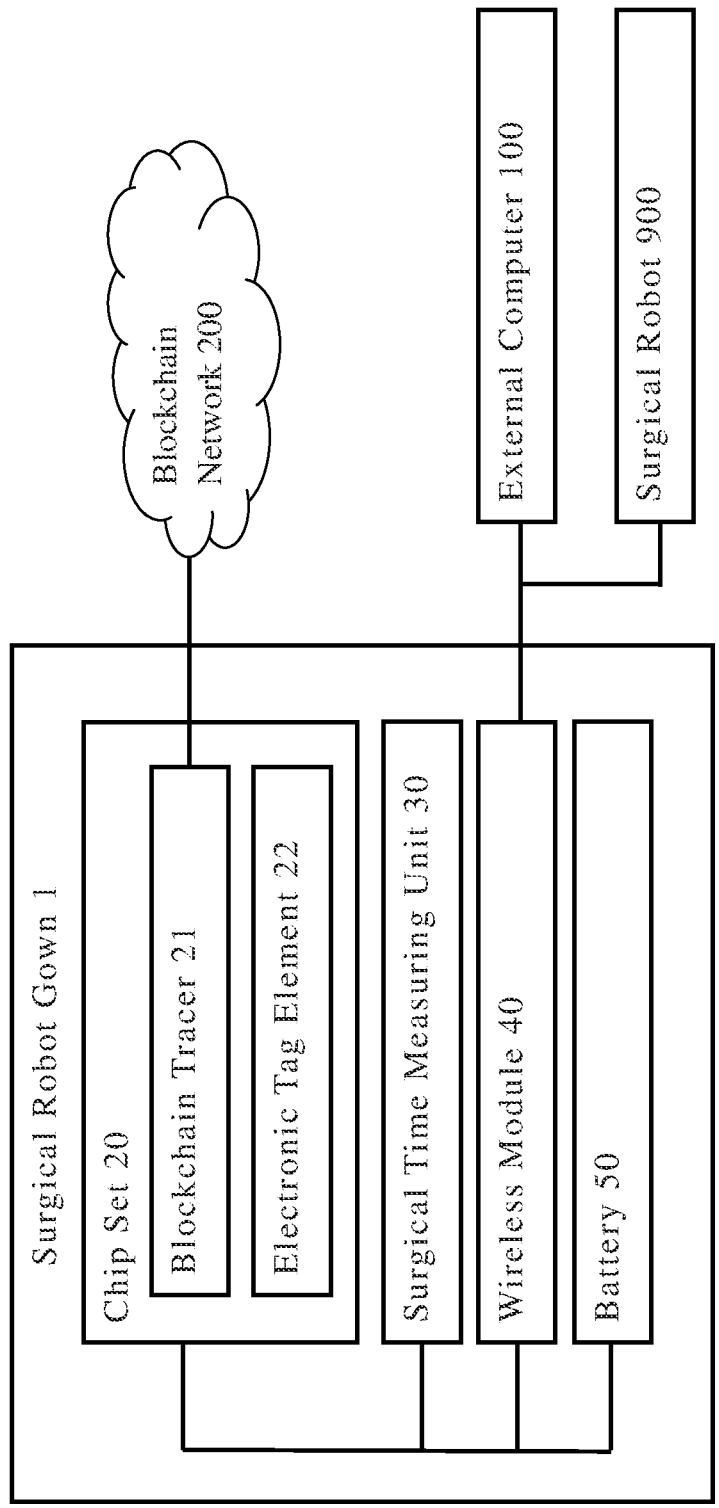
FIG. 3 is a system architecture diagram of the surgical robot gown, the surgical robot, the external computer and the blockchain network in an embodiment of the present invention.

Referring to FIG. 1 to FIG. 3 for the surgical robot gown of an embodiment of the present invention. FIG. 1 is a schematic diagram of a surgical robot gown in an embodiment of the present invention; FIG. 2 is a schematic diagram of the surgical robot gown applied to the surgical robot in an embodiment of the present invention; FIG. 3 is a system architecture diagram of the surgical robot gown, the surgical robot, the external computer and the blockchain network in an embodiment of the present invention.

As shown in FIG. 1 to FIG. 3, in an embodiment of the present invention, the surgical robot gown 1 is applied to a surgical robot 900, which can prevent the surgical robot 900 from being splashed and damaged by body fluids during the surgery, and the surgical robot gown 1 is electrically connected to a blockchain network 200. The surgical robot 900 includes a scalpel 910 and a robotic arm 920. The scalpel 910 is connected to the robotic arm 920 to perform surgery on the patient. The robotic arm 920 is a precision machine with a mobile function to drive the scalpel 910 to a position suitable for surgery.

In an embodiment of the present invention, the surgical robot gown 1 includes a waterproof gown 10, a chip set 20, a surgical time measuring unit 30, a wireless module 40, and a battery 50. The waterproof gown 10 is made of a decomposable material with waterproof and antibacterial effects, such as thermoplastic urethane (TPU). However, the material of the waterproof gown 10 is not limited to this. The waterproof gown covers the robot arm 920 and allows the scalpel 910 to expose from the waterproof gown 10 to the outside. The waterproof gown 10 includes a cuff 11, which is, for example, an opening provided with an elastic band to produce a converging function. The scalpel 910 is exposed to the outside from the cuff 11, and the cuff 11 can be tightened at the connection between the scalpel 910 and the robotic arm 920 to prevent the patient's body fluid from being sprayed to the robotic arm 920.

In an embodiment of the present invention, the chip set 20 is arranged on the waterproof gown 10, and the chip set 20 includes a blockchain tracer 21 and an electronic tag element 22. The blockchain tracer 21 is a computing chip, which is electrically connected to a blockchain network 200. The blockchain tracer 21 is used for recording the operation data of the surgical robot 900 in the blockchain network 200. In this way, with the characteristics of the blockchain that is traceable and not easily tampered with, the operation data can be recorded and tracked. According to one embodiment of the present invention, the data of the operation performed by the surgical robot 900 includes a power-on time, a power-off time, a type of operation, and a patient data. However, the type of operation data is not limited to this. In addition, the data of the operation performed by the surgical robot 900 can also be entered into the blockchain tracer 21 through the external computer 100, and then recorded in the blockchain network 200 through the blockchain tracer 21. The electronic tag element 22 records the information of the surgical robot gown 1 by means of radio frequency identification, such as the information of the model of the surgical robot gown 1, the service life of the waterproof gown 10, and the applicable model of the surgical robot 900, etc. The information recorded by the electronic tag element 22 can be input by the external computer 100. However, the information of surgical robot gown 1 is not limited to the above, and can be altered according to design requirements.

In an embodiment of the present invention, the surgical time measuring unit 30 is arranged on the waterproof gown 10 and electrically connected to the chip set 20. The surgical time measuring unit 30 is a chip with an operation time measurement function, and is used to measure an operation time of the surgical robot 900. The operation time includes an operation start time and an operation end time. With the operation time measurement function of the surgical time measuring unit 30, the detailed operation time of the surgical robot 900 can be confirmed.

In an embodiment of the present invention, the wireless module 40 is, for example, a network chip. The wireless module 40 is arranged on the waterproof gown 10 and electrically connected to the chip set 20, the surgical time measuring unit 30, the external computer 100, and the surgical robot 900. The wireless module 40 is used for transmitting the information measured by the chip set 20 and the surgical time measuring unit 30 to the external computer 100, so that the medical staff can operate the external computer 100 to understand the data of the surgical robot gown 1.

In an embodiment of the present invention, the battery 50 is arranged in the waterproof gown 10, and provides power to the chip set 20, the surgical time measuring unit 30, and the wireless module 40 to ensure power supply to the chip set 20, the surgical time measuring unit 30, and the wireless module for normal operation.

As shown in FIG. 1 to FIG. 3, before the surgical robot 900 conducts the surgery, the medical staff can first put the surgical robot gown 1 on the surgical robot 900 to allow the waterproof gown 10 having waterproof and antibacterial effects to cover the robotic arm 920, and allow the scalpel 910 to be exposed from the cuff 11 to the outside of the waterproof gown 10. The cuff 11 can be tightened on one end of the scalpel 910 to prevent the patient's body fluid from being sprayed to the robotic arm 920, so that the robotic arm 920 can be prevented from being damaged by body fluid splashing during the surgery.

Next, when the surgical robot 900 performs an operation, the surgical time measuring unit 30 is connected to the surgical robot 900 through the wireless module 40 to measure the operation start time and the operation end time. With the operation time measurement function of the surgical time measuring unit 30, detailed operation time of the surgical robot 900 can be confirmed.

In addition, the medical staff can also operate the external computer 100 to connect to the wireless module 40 in order to input the information of the surgical robot gown 1 by radio frequency identification to the electronic tag element 22, such as the information of the model of the surgical robot gown 1, the service life of the waterproof gown 10, and the applicable model of the surgical robot 900. In this way, in the future, the medical staff can use a radio frequency identification reader to read the data recorded in the electronic tag element 22 to quickly understand the relevant information of the surgical robot gown 1.

Furthermore, the medical staff can also operate the external computer 100 to input the data of the operation performed by the surgical robot 900 into the blockchain tracer 21, and then use the blockchain tracer 21 to record the operation data of the surgical robot 900 on the blockchain network 200. With the function of tracing the event history of the blockchain, operation data such as the power-on time, the power-off time, the type of operation, and the patient data, etc. performed by the surgical robot 900 can be recorded in the blockchain network 200. In this way, the event history of the operation performed by the surgical robot 900 can be clearly recorded and managed by the blockchain, which has characteristics of record tracing and not easily being tampered with.

With the design of the surgical robot gown 1 of the present invention, the surgical robot gown 1 has diversified and convenient functions, such as tracing the event history of the surgical robot performing the surgery, and recording the surgical robot gown 1 by radio frequency identification, so that the medical staff can quickly read the data, confirm the detailed operation time of the surgical robot, and prevent the surgical robot from being damaged by body fluid splashing during the operation. The waterproof gown is made of decomposable materials, which can be decomposed by microorganisms in the natural environment, so it has an effect of environmental protection.

Although the invention has been explained in relation to its preferred embodiment, it is to be understood that many other possible modifications and variations can be made without departing from the spirit and scope of the invention as hereinafter claimed.

What is claimed is:

1. A surgical robot gown, applied to a surgical robot and electrically connected with a blockchain network, wherein the surgical robot comprises a scalpel and a robotic arm, the surgical robot gown comprising:
   a waterproof gown, covering the robotic arm and exposing the scalpel from the waterproof gown to an outside;
   a chip set, arranged on the waterproof gown, wherein the chip set comprises a blockchain tracer for recording the surgery data in the blockchain network for tracing; and
   an operation time measuring unit, arranged on the waterproof gown and electrically connected to the chip set for measuring a surgery time of the surgical robot.

2. The surgical robot gown defined in claim 1, wherein the chip set further comprises an electronic tag element, which records an information of the surgical robot gown by means of a radio frequency identification.

3. The surgical robot gown defined in claim 2, wherein the surgical robot gown further comprises a wireless module, which is arranged on the waterproof gown and electrically connected to the chip set, the surgical time measuring unit and an external computer.

4. The surgical robot gown defined in claim 3, wherein the surgical robot gown further comprises a battery, which is arranged on the waterproof gown and provides power to the chip set, the surgical time measuring unit, and the wireless module.

5. The surgical robot gown defined in claim 4, wherein the waterproof gown further comprises a cuff, from which the scalpel is exposed to the outside.

6. The surgical robot gown defined in claim 5, wherein the waterproof gown is made of thermoplastic urethane (TPU).

7. The surgical robot gown defined in claim 6, wherein the operation time comprises an operation start time and an operation end time.

8. The surgical robot gown defined in claim 7, wherein a data of an operation performed by the surgical robot comprises a power-on time, a power-off time, a type of surgery, and a patient data.

\* \* \* \* \*